(12) United States Patent
Green-Tucker

(10) Patent No.: US 9,056,065 B1
(45) Date of Patent: Jun. 16, 2015

(54) HAIR COMPOSITE

(71) Applicant: Shawnee Green-Tucker, Bedford, OH (US)

(72) Inventor: Shawnee Green-Tucker, Bedford, OH (US)

( * ) Notice: Subject to any disclaimer, the term of this patent is extended or adjusted under 35 U.S.C. 154(b) by 0 days.

(21) Appl. No.: 14/165,111

(22) Filed: Jan. 27, 2014

(51) Int. Cl.
| | |
|---|---|
| *A61K 8/97* | (2006.01) |
| *A61Q 5/06* | (2006.01) |
| *A61Q 7/00* | (2006.01) |
| *A61K 36/00* | (2006.01) |
| *A61K 36/28* | (2006.01) |
| *A61K 36/61* | (2006.01) |
| *A61K 36/53* | (2006.01) |

(52) U.S. Cl.
CPC ... *A61K 8/97* (2013.01); *A61Q 5/06* (2013.01); *A61Q 7/00* (2013.01); *A61K 36/00* (2013.01); *A61K 36/28* (2013.01); *A61K 36/61* (2013.01); *A61K 36/53* (2013.01)

(58) Field of Classification Search
CPC ....... A61K 36/00; A61K 36/28; A61K 36/53; A61K 36/61
USPC ........................................................ 424/725
See application file for complete search history.

(56) References Cited

U.S. PATENT DOCUMENTS

| | | | |
|---|---|---|---|
| 6,058,943 A | 5/2000 | Davis-Harris | |
| 6,488,920 B1 | 12/2002 | Thomas | |
| 6,861,077 B1 | 3/2005 | Cannell et al. | |
| 2013/0266674 A1 | 10/2013 | Hall | |

OTHER PUBLICATIONS

Esoteric Oils: Isoprene units; pp. 1-4; published in US.
The Fine Art of Protein and Moisture Balancing for Black Hair Care; Audrey Davis-Sivasothy, author; Jun. 18, 2007 (article): published, Houston, Texas.
10 Secrets to Growing Black Hair Long and Fast; C. Collins, author; Copyright 2012 Embrace Your Natural Hair (booklet), Retrieved Jan. 2014 http://www.Embraceyournaturalhair.com.

*Primary Examiner* — Michael Meller

(57) ABSTRACT

One or more hair care products and/or techniques for creating such hair care products are provided. For example, a hair care product comprises one or more carriers, such as a coconut oil, an evening primrose, and/or a hemp oil. The hair care product comprises one or more oils, such as a lavender oil, a tee tree oil, a nettle leaf oil, a horsetail extract, a clary sage oil, a rosemary oil, a basil oil, a lemongrass oil, a cypress oil, a cinnamon leaf oil, and/or a roman chamomile. The hair care product may be used for restructuring (e.g., relaxing) a natural growth pattern of hair. The hair care product may stimulate hair follicles so that protein and/or moisturizing portions of the hair care product may seep into the scalp for growing and sustaining healthy hair. The hair care product may treat or mitigate eczema, dryness, breakage, sores, and/or fungal bacteria.

2 Claims, 2 Drawing Sheets

HAIR COMPOSITE

TECHNICAL FIELD

The instant application is generally directed towards hair care compositions for improving scalp health, hair growth, and/or hair pattern transformation, such as hair relaxing.

BACKGROUND

Various products are available for hair care, such as shampoos, conditioners, hair spray, waxes, hair straighteners and relaxers, hair growth promotion products, gels, etc. In an example, a user may have lost hair for various reasons, such as hair follicle damage, lack or loss of nutrients, a medical condition, stress, hereditary reasons, and/or a variety of other reasons. Accordingly, the user may utilize a hair growth promotion product in an attempt to promote hair growth to compensate for the hair loss. In another example, a user with relatively curly hair may utilize a hair relaxer product to straighten curly hair (e.g., to improve effectiveness of moisturizers and growth).

SUMMARY

This summary is provided to introduce a selection of concepts in a simplified form that are further described below in the detailed description. This summary is not intended to identify key factors or essential features of the claimed subject matter, nor is it intended to be used to limit the scope of the claimed subject matter.

Among other things, one or more hair care products and/or techniques for creating such hair care products are provided herein. A hair care product comprises a set carrier oils. The set of carrier oils comprise a coconut oil (*Cocos nucifera*), an evening primrose (*Oenothera biennis*), a hemp oil (*Cammabis sativa* L.), or any other suitable carrier oil. In an example, the set of carrier oils comprises the coconut oil in an amount between about 1 liter to about 2.2 liters by volume, an amount between about 0.1 liters to about 0.24 liters by volume, or any other amount. In an example, the set of carrier oils comprises the hemp oil in an amount between about 500 ml to about 1000 ml by volume, an amount between about 40 ml to about 80 ml by volume, or any other amount. In an example, the set of carrier oils comprises the evening primrose in an amount between about 80 ml to about 160 ml by volume, an amount between about 10 ml to about 30 ml by volume, or any other amount.

The hair care product comprises a set of oils. The set of oils comprise a lavender oil (*lavandula angustifolia*), a tee tree oil (*melaleuca*), a nettle leaf oil (*urtica dioica*), a horsetail extract (*Equisetum arvense* L/Herbs *Equiseti arbensisand*), a clary sage oil (*salvia sclarea*), a rosemary oil (*rosmarinus*), a basil oil (*ocimum basilicum*), a lemongrass oil (*cymbopogon marginatus*), a cypress oil (cupressaceae), a cinnamon leaf oil (*Cinnamomum zeylanicum*), a roman chamomile (*Chamaemelum nobile*), and/or any other suitable oil. In an example, the set of oils comprises at least one of the lavender oil in an amount between about 7 ml to about 7.8 ml by volume, the tee tree oil in an amount between about 20 ml to about 40 ml by volume, the nettle leaf oil in an amount between about 20 ml to about 40 ml by volume, the horsetail extract in an amount between about 20 ml to about 40 ml by volume, the clary sage oil in an amount between about 5 ml to about 15 ml by volume, the rosemary oil in an amount between about 5 ml to about 15 ml by volume, the basil oil in an amount between about 5 ml to about 15 ml by volume, the lemongrass oil in an amount between about 5 ml to about 15 ml by volume, the cypress oil in an amount between about 5 ml to about 15 ml by volume, the cinnamon leaf oil in an amount between about 10 ml to about 20 ml by volume, the roman chamomile in an amount between about 10 ml to about 20 ml by volume, or any other suitable oil or amount thereof.

In another example, the set of oils comprises at least one of the lavender oil in an amount between about 0.02 ml to about 0.06 ml by volume, the tee tree oil in an amount between about 0.04 ml to about 0.08 ml by volume, the nettle leaf oil in an amount between about 0.04 ml to about 0.08 ml by volume, the horsetail extract in an amount between about 0.01 ml to about 0.05 ml by volume, the clary sage oil in an amount between about 0.02 ml to about 0.06 ml by volume, the rosemary oil in an amount between about 0.02 ml to about 0.06 ml by volume, the basil oil in an amount between about 0.02 ml to about 0.06 ml by volume, the lemongrass oil in an amount between about 0.02 ml to about 0.04 ml by volume, the cypress oil in an amount between about 0.02 ml to about 0.04 ml by volume, the cinnamon leaf oil in an amount between about 0.01 ml to about 0.03 ml by volume, the roman chamomile in an amount between about 0.01 ml to about 0.03 ml by volume, or any other suitable oil or amount thereof. It may be appreciated that the set of carrier oils and/or the set of oils may comprise carrier oils and/or oils in any amount, and that the examples provided are not meant to be limiting.

To the accomplishment of the foregoing and related ends, the following description and annexed drawings set forth certain illustrative aspects and implementations. These are indicative of but a few of the various ways in which one or more aspects may be employed. Other aspects, advantages, and novel features of the disclosure will become apparent from the following detailed description when considered in conjunction with the annexed drawings.

DETAILED DESCRIPTION

Figure 1:
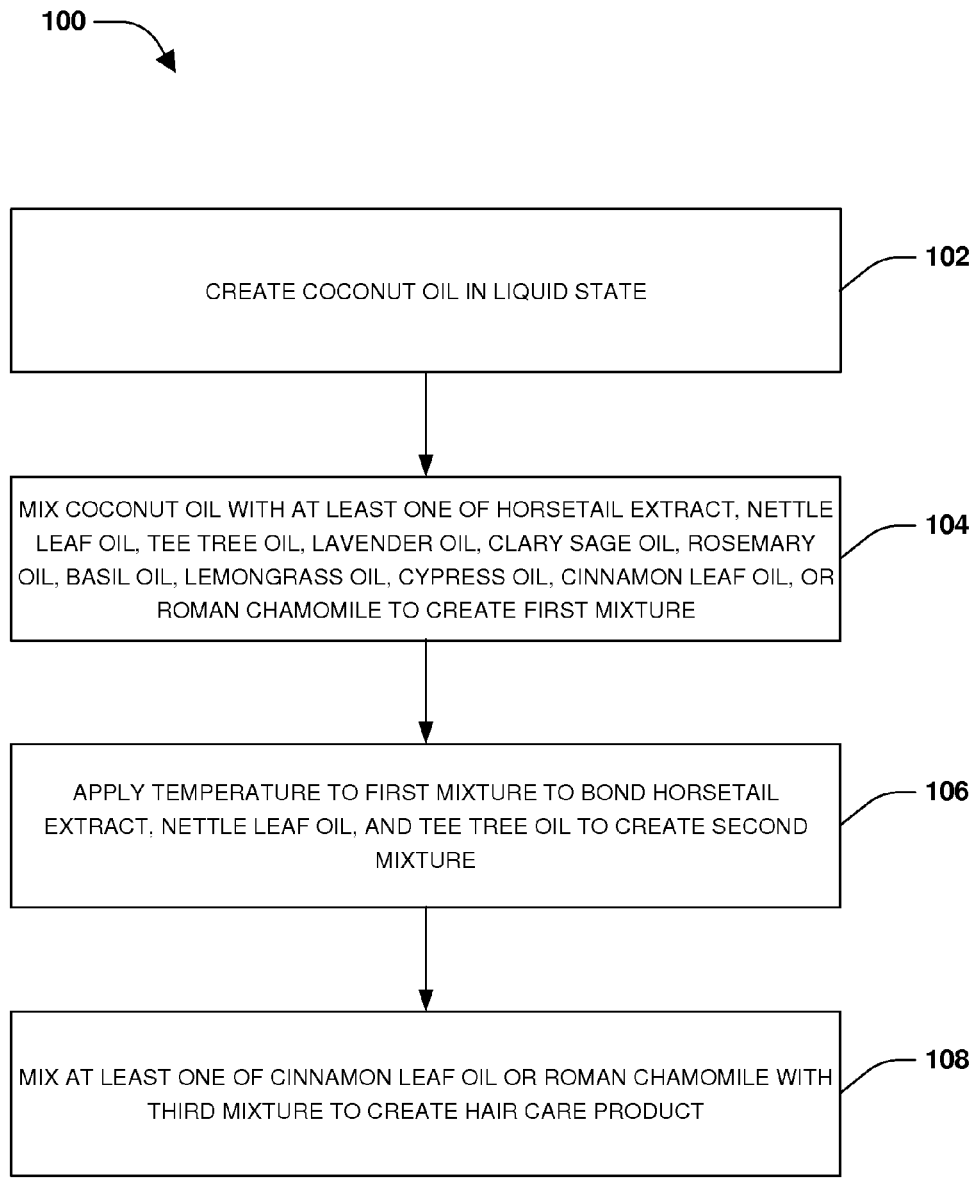
FIG. 1 is a flow diagram illustrating an exemplary method of creating a hair care product.

The claimed subject matter is now described with reference to the drawings, wherein like reference numerals are generally used to refer to like elements throughout. In the following description, for purposes of explanation, numerous specific details are set forth in order to provide an understanding of the claimed subject matter. It may be evident, however, that the claimed subject matter may be practiced without these specific details. In other instances, structures and devices are illustrated in block diagram form in order to facilitate describing the claimed subject matter.

Figure 2:
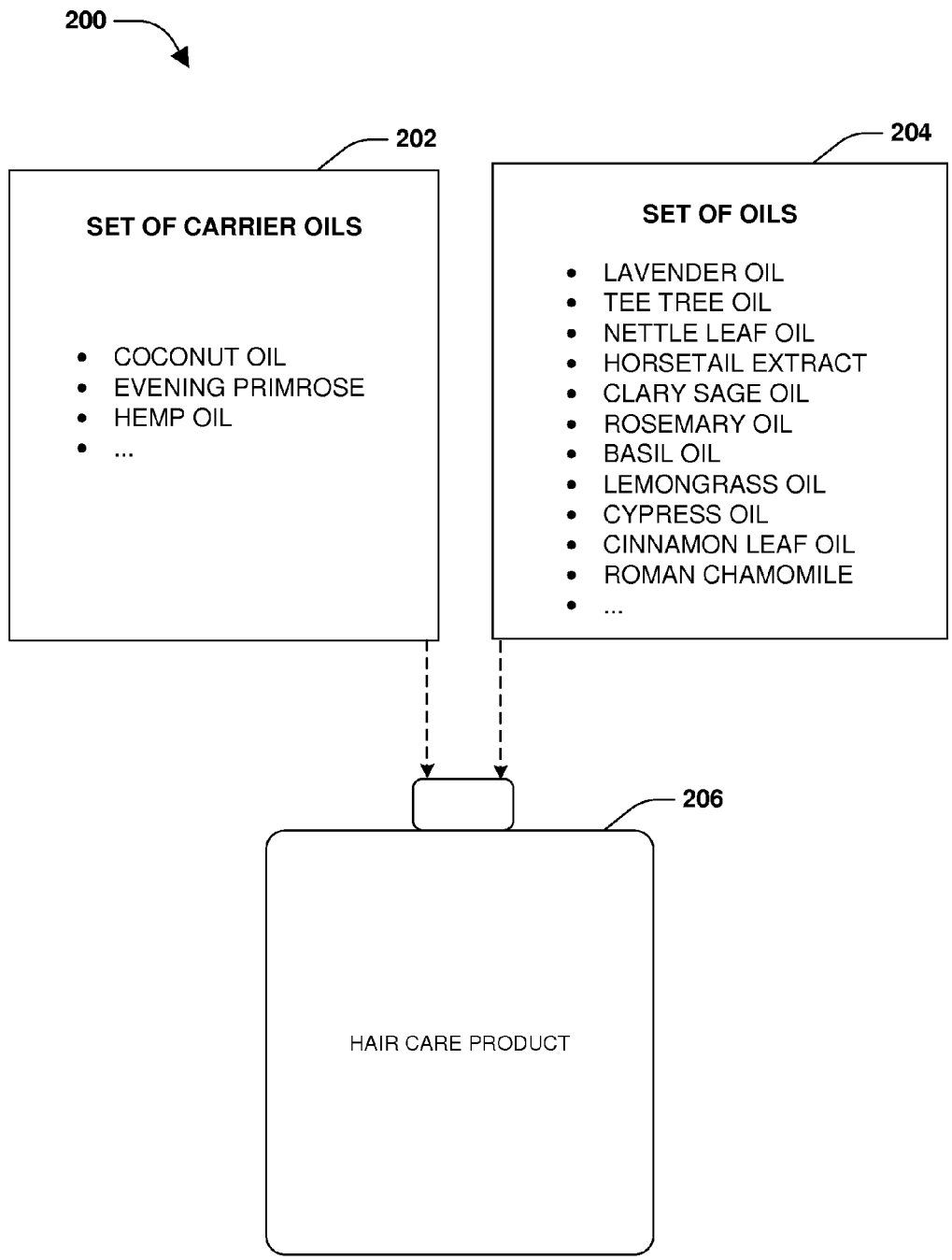
FIG. 2 is an illustration of an example of a hair care product.

One or more hair care products and/or techniques for creating such hair care products are provided. In an example, the hair care product 206 comprises a set carrier oils 202, such as a coconut oil, an evening primrose, a hemp oil, or any other suitable carrier oil, as illustrated in example 200 of FIG. 2. The hair care product 206 comprises a set of oils 204, such as a lavender oil, a tee tree oil, a nettle leaf oil, a horsetail extract, a clary sage oil, a rosemary oil, a basil oil, a lemongrass oil, a cypress oil, a cinnamon leaf oil, a roman chamomile, and/or any other suitable oil.

The hair care product promotes hair growth by restructuring the natural hair pattern, such as at the root of the scalp, to allow the root and hair to absorb protein and/or moisture that promotes hair growth. For example, the hair care product promotes the absorption of a protein, such as keratin, to add strength, shine, and/or protection again hair breakage (e.g., relatively curly hair may otherwise be prone to breaking, drying, and/or damage because the curly texture does not allow oils to adequately spread from the scalp to ends of hair strands). The protein may add elasticity to the hair, which may compensate for a lack of elasticity due to hair having an inadequate amount of protein, such as curly hair. Because the hair care product may comprise natural oils, hair dehydration and/or breakage resulting from chemical-based products such as hair relaxers used to relax curly texture of hair is mitigated.

In an example, the combination of coconut oil (e.g., extra virgin coconut oil), hemp oil, evening primrose, and at least one of lavender oil, clary sage oil, basil oil, lemongrass oil, rosemary oil, horsetail oil, cinnamon leaf oil, roman chamomile, or cypress oil provides a spicy aroma, mitigates or corrects disease and bacteria, and/or simulates the scalp and hair follicles to grow and strengthen. The hair care product provides protein to hair follicles, which may restructure (e.g., relax) hair strands without utilizing harmful and/or synthetic chemicals (e.g., based upon natural oils, such as essential oils, comprised within the hair care product). Providing protein to hair follicles may relax the hair follicles so that the hair follicles may be relative more susceptible to receiving and/or retaining moisture. The hair care product stimulates the roots to absorb and/or retain moisture from the set of oils, which may mitigate breakage, damage, shortening, dryness, and/or itchy scalp. The hair care product may be applied to a scalp, hair, and/or a body of the user. In an example, the hair care product may promote hair growth and/or hair thickening based upon routine utilization (e.g., use for three or more consecutive weeks).

In some embodiments, a hair care product comprises a set of carrier oils. The set of carrier oils comprises at least one of a coconut oil, an evening primrose, or a hemp oil. In an example, the set of carrier oils comprises at least two of the coconut oil, the evening primrose, or the hemp oil. In an example, the set of carrier oils comprises the coconut oil, the evening primrose, and the hemp oil. In an example, the set of carrier oils comprises the coconut oil in an amount between about 1 liter to about 2.2 liters by volume, an amount between about 0.1 liters to about 0.24 liters by volume, or any other amount. In an example, the set of carrier oils comprises the hemp oil in an amount between about 500 ml to about 1000 ml by volume, an amount between about 40 ml to about 80 ml by volume, or any other amount. In an example, the set of carrier oils comprises the evening primrose in an amount between about 80 ml to about 160 ml by volume, an amount between about 10 ml to about 30 ml by volume, or any other amount.

The hair care product comprises a set of oils (e.g., natural oils, essential oils, and/or any other type of oils). The set of oils comprises a lavender oil, a tee tree oil, a nettle leaf oil, a horsetail extract, a clary sage oil, a rosemary oil, a basil oil, a lemongrass oil, a cypress oil, a cinnamon leaf oil, a roman chamomile, and/or any other suitable oil. It may be appreciated that the set of oils may comprise any number of (e.g., at least five of) the lavender oil, the tee tree oil, the nettle leaf oil, the horsetail extract, the clary sage oil, the rosemary oil, the basil oil, the lemongrass oil, the cypress oil, the cinnamon leaf oil, or the roman chamomile. In an example, the set of oils comprises at least one of the lavender oil in an amount between about 7 ml to about 7.8 ml by volume, the tee tree oil in an amount between about 20 ml to about 40 ml by volume, the nettle leaf oil in an amount between about 20 ml to about 40 ml by volume, the horsetail extract in an amount between about 20 ml to about 40 ml by volume, the clary sage oil in an amount between about 5 ml to about 15 ml by volume, the rosemary oil in an amount between about 5 ml to about 15 ml by volume, a basil oil in an amount between about 5 ml to about 15 ml by volume, the lemongrass oil in an amount between about 5 ml to about 15 ml by volume, the cypress oil in an amount between about 5 ml to about 15 ml by volume, the cinnamon leaf oil in an amount between about 10 ml to about 20 ml by volume, the roman chamomile in an amount between about 10 ml to about 20 ml by volume, or any other suitable oil.

In another example, the set of oils comprises at least one of the lavender oil in an amount between about 0.02 ml to about 0.06 ml by volume, the tee tree oil in an amount between about 0.04 ml to about 0.08 ml by volume, the nettle leaf oil in an amount between about 0.04 ml to about 0.08 ml by volume, the horsetail extract in an amount between about 0.01 ml to about 0.05 ml by volume, the clary sage oil in an amount between about 0.02 ml to about 0.06 ml by volume, the rosemary oil in an amount between about 0.02 ml to about 0.06 ml by volume, the basil oil in an amount between about 0.02 ml to about 0.06 ml by volume, the lemongrass oil in an amount between about 0.02 ml to about 0.04 ml by volume, the cypress oil in an amount between about 0.02 ml to about 0.04 ml by volume, the cinnamon leaf oil in an amount between about 0.01 ml to about 0.03 ml by volume, the roman chamomile in an amount between about 0.01 ml to about 0.03 ml by volume, or any other suitable oil.

An embodiment of creating a hair care product is illustrated by an exemplary method 100 of FIG. 1. At 102, a coconut oil (e.g., an extra virgin coconut oil) is created in a liquid state. For example, a temperature (e.g., a temperature above room temperature) is applied to the coconut oil, while in a solid state, to create the coconut oil in the liquid state (e.g., heat is applied by a microwave or other heating device for between about 2 minutes to about 6 minutes). In an example, the coconut oil, in the liquid state, is shaken or stirred (e.g., vigorously shaken by hand or by a mechanical device).

At 104, the coconut oil (e.g., in the liquid state) is mixed with at least one of a horsetail extract, a nettle leaf oil, a tee tree oil, a lavender oil, a clary sage oil, a rosemary oil, a basil oil, a lemongrass oil, a cypress oil, a cinnamon leaf oil, or a roman chamomile oil to create a first mixture (e.g., the horsetail extract, the nettle leaf oil, the tee tree oil are mixed with at least one of the lavender oil, the clary sage oil, the rosemary oil, the basil oil, the lemongrass oil, the cypress oil, the cinnamon leaf oil, or the roman chamomile oil to create the first mixture). In an example, the first mixture is blended together (e.g., vigorously shaken by hand or by a mechanical device).

At 106, a temperature (e.g., a temperature below room temperature) is applied to the first mixture to bond the horsetail extract, the nettle leaf oil, and the tee tree oil together to create a second mixture. In an example, the first mixture is frozen (e.g., frozen for 1 or more hours, such as about 12 hours). In an example, one or more metal structures (e.g., 6 metal structures, such as ⅛ inch metal balls, and/or a metal strainer structure such as a 1 inch metal strainer ball) may be added to the first mixture, which may then be frozen. The relatively colder temperature may cause a chemical reaction of horsetail extract molecular elements, nettle leaf oil molecular elements, and/or tee tree oil molecular elements, which may form one or more bonded objects (e.g., spherical balls comprising at least some of the horsetail extract, the nettle leaf oil, the tee tree oil, and/or portions thereof). In an example where the first mixture is in the frozen state, a second temperature (e.g., a temperature above freezing, such as above room temperature, may be applied for 3 to 5 minutes)

is applied to the first mixture to melt the first mixture into a liquid solution, which may be shaken or blended. In this way, the second mixture is created.

At 108, hemp oil and/or evening primrose are mixed with the second mixture to create a third mixture comprising the hair care product. In an example, the cinnamon leaf oil and/or the roman chamomile are added to the third mixture to create the hair care product. In an example the third mixture is blended. In an example, the third mixture is strained to remove the one or more bonded objects from the third mixture to create the hair care product. In an example, the third mixture may be refrozen, processed (e.g., vigorously shaken with one or more metal structures, such as 6 metal structures and/or a metal strainer structure such as a 1 inch metal strainer ball) and/or restrained one or more times to create the hair care product. In this way, the hair care product is created.

Many compounds found in oils are terpeniod molecules with the starting point of the chemical element carbon isoprene which comprises 5-40 units. These essential carbon atoms are as such: Hemiterpenes=1 isoprene unit with 5 carbon atoms; monoterpenes=2 isoprene unit with 10 carbon atoms; sesquiterpenes=3 isoprene unit with 15 carbon atoms; diterpenes=4 isoprene unit with 20 carbon atoms; triterpenes=6 isoprene unit with 30 carbon atoms; and tetraterpenes=8 isoprene unit with 40 carbon atoms. However, isoprene may not comprise terpene, but terpenes may consist of isoprene units which are found in the plant material itself, or in the extraction process of the set of oils (e.g., a natural oil).

In an example, the hair care product comprises the set of oils that may comprise unsaturated hydrocarbons (e.g., with the structure based on the isoprene unit known as terpene hydrocarbons) and/or oxygenated compounds. These compounds may comprise alcohol, esters, aldehydes, ketones, lactones, coumarins, ethers, oxides, and/or a variety of other compounds. When selecting oils for the set of oils, various considerations may be taken into account, such as which isoprene unit interacts with what carbon atom, and how much by volume and/or percentage may be used.

In an example of terpenes hydrocarbons, monoterpene compounds are found in oils and have a structure 10 carbon atoms with at least two isoprene units. These components have anti-inflammatory, antiseptic, antiviral, and antibacterial therapeutic properties. Sequiterpenes comprise 15 carbon atoms and have compounds that are derived from the Roman chamomile. The monoterpene compounds possess an anti-inflammatory and/or anti-allergy properties.

In an example of oxygenated compounds, Monoterpene alcohol may comprise linalool, citronellol, and/or terpineol found in lavender and tea tree oil. These properties are may be used as an antiseptic, anti-viral, anti-fungal, and/or energy. Tea tree oil may be used to treat symptoms associated with dry scalp as well as oily hair.

In an example of aldehydes, aldehydes is an unstable molecule causing it to oxidize, quickly, in the presence of oxygen or low heat. However, when combined with at least one oil within the set of oils, aldehydes give off a citrus-like fragrance found in lemongrass and cinnamon leaf. This compound may react when dilution is low, such as around 1% or lower, in its original state. Aldehydes may be used for the purpose of anti-fungal, anti-inflammatory, disinfectant, sedative, and/or an uplifting therapeutic effect.

In an example of ketones, ketones may be used as a therapeutic treatment because of mucolytic (e.g., mucus easing) properties that regenerates the skin tissues caused by wounds, scaring, stretching, and adhesions. This atomic compound is prominent in the properties of rosemary.

In an example of esters, the esters molecule compound may be formed of alcohols and/or acids, and may tend to have a fruity fragrance. The esters has a therapeutic effect because of its fruity component. The esters may be used as a sedative, an antispasmodic, an anti-fungal, and/or an anti-microbial agent. In an example, esters may be linalyl acetate, which are found in lavender and clary sage.

In an example of ethers, phenolic ethers are the found in oils with anethol and/or methyl chavicol, which is found in basil. Ethers have properties that are used for analgesic and/or antimicrobial.

In an example of oxides, oxides may be the therapeutic effect of expectorant, with 1, 8-cineole, commonly known as eucalyptol and found in the atomic element properties of rosemary.

Roman chamomile oil is produced from *Anthemis nobilis* (*Chamaemelum nobile*) of the family species Asteraceae, formerly placed in the Compositae family. It is also known as English chamomile, sweet chamomile and garden chamomile. The main chemical compounds of this composite are α-pinene, camphene, b-pinene, savinene, myrcene, 1.8-cineole, y-terpinene, caryophyllene, and propyl angelate, and butyl angelate. The blend of these chemical atoms produces a molecular effect that is non-toxic and non-irritant, yet have properties that are used as analgesic, anti-spasmodic, antibiotic, anti-inflammatory, anti-infectious, anti-depressant, anti-neuralgic, antipholgistic, antiseptic, antispasmodic, bactericidal, carminative, cholagogue, cicatrisant, emmenagogue, febrifuge, hepactic, sedative, nervine, digestive, tonic, sudorific, stomachic, vermifuge, and vulnerary. Roman chamomile oil is extracted from flowers by steam distillation, with the Roman chamomile yielding about 1.7% from its fresh flowers. Roman chamomile essential oil produces a sweet, apple-like fragrance and is very light blue in color and light in density, with watery viscosity.

Cinnamon leaf oil is extracted from *Cinnamomum zeylanicum* (also known as *C. verum* and *Laurus cinnamomum*) of the Lauraceae family. It is also referred to as Ceylon, Madagascar, Seychelles or true cinnamon. The flavor of cinnamon is due to an aromatic essential oil that makes up between about 0.5% to about 2% of its composition. The cinnamon leaf oil is prepared by roughly pounding the bark, macerating it in sea water, and then quickly distilling the whole. The cinnamon leaf oil is of a golden-yellow color, with the characteristic odor of cinnamon and a very hot aromatic taste. The pungent taste and scent come from cinnamic aldehyde or cinnamaldehyde (about 90% of the essential oil from the bark) and, by reaction with oxygen as it ages, it darkens in color and forms resinous compounds. Other chemical components of the cinnamon leaf oil comprise ethyl cinnamate, eugenol (found mostly in the leaves), beta-caryophyllene, linalool, and methyl chavicol. The leaves and twigs or inner dried bark are subjected to steam distillation. The leaves yield between about 1.6-1.8% and the bark yields between about 0.5-1.00% oil. The main chemical components of the cinnamon leaf oil, which may be obtained from the leaves, are eugenol, eugenol acetate, cinnamic aldehyde and benzyl benzoate. The therapeutic properties of cinnamon oil are analgesic, antiseptic, antibiotic, antispasmodic, aphrodisiac, astringent, cardiac, carminative, emmenagogue, insecticide, stimulant, stomachic, tonic, and vermifuge. Cinnamon leaf oil is known for its therapeutic chemical components such as analgesic, antiseptic, antibiotic, antispasmodic, aphrodisiac, astringent, cardiac, carminative, emmenagogue, insecticide, stimulant, stomachic, tonic, and vermifuge.

In an example of nettles, nettles may comprise acetylcholine, histamine, and formic acid. Formic acid is the same acid that ants have in their saliva glands. Other chemicals found in the hairs of the nettle stem or leaves are silica, serotonin, and 5-hydroxy tryptamine and lectins (proteins). Many of these chemicals are smooth muscle stimulants. This lectins differ from all the other plant lectins due to its molecular structure. The properties of nettles have been shown to possess both antifungal and insecticidal activity and to act synergistically with chitinase in inhibiting fungal growth. It was also shown to directly inhibit cell proliferation and block the binding of epidermal growth factor to its receptor on a tumor cell line.

In an example of cypress, atomic components of cypress may be a-pinene, camphene, sabinene, b-pinene, d-3carene, myrcene, a-terpinene, linalool, bornyl acetate, cedrol, and cadinene. Cypress molecular structure is used for calming and soothing effects on irritability, anger, stress, vasoconstrictor on varicose veins and hemorrhoids, respiratory difficulty, asthma, arthritis, rheumatic pain, skin wounds, and influenza.

In an example of coconut oil, coconut oil may be an atomic compound used in Ayurvedic medicine, is an edible oil, and may be extracted from kernel or meal of matured coconuts from coconut palm (*Cocos nucifera*). Coconut oil is highly saturated in fat content and is slow to oxidize. However, the hair care product may comprise virgin coconut oil as a carrier oil because the virgin coconut oil comprises medium-chain triglycerides, which may not carry the same highly saturated fat content as the matured coconut oil. The use of coconut oil can increase protein content and may decrease hair loss due to its content of medium chain triglycerides (MCT). Coconut oil is able to penetrate the interior of the hair shaft, due to its light molecular weight. In addition, coconut oil protects the hair, and it is harmless to the humans scalp and body.

In an example of hemp oil, hemp oil is valued for its nutritional properties as well as for the health benefits associated with it. Hemp oil has a chemical balance of essential fatty acid, linoleic acid, α-linoleic acid, β-sitosterol, cannabinoids, that even makes its a functional food for human consumption. Although its fatty acid composition is most often noted, with oil content ranging from 25%-35%, is an additional comprised of approximately 20%-25% protein, 20%-30% carbohydrates, and 10%-15% fiber, along with an array of trace minerals. Due to hemp oil's multiple composite of molecules it has be shown an exhibit for pharmacological activities such as anti-cancer byproducts, anti-inflammatory, and anti-thrombotic properties. Hemp oil is known for omega-3 PUFA which helps increase general metabolic rates and promote the burning of fat.

In an example of primrose, primrose comprises oleic acid (e.g., linoleic acid, alpha-linoleic acid, beta-linoleic acid, gamma-linoleic acid (GLA), stearic acid, aspartic acid, glutamine, palmitic (seeds) caffeic, ellagic, and/or p-coumaric), amino acids (e.g., arginine, cysteine, phenylalanine, glycine, histamine, isoleucine, lucien, lysine, proline, lysine, threonine, tyrosine, and/or valine), and/or vitamins (e.g., ascorbic acid (Vitamin C), fiber, minerals: Potassium, magnesium, manganese, ammonia, copper, boron, iron, zinc, calcium, and/or phosphorus), etc. Primrose Oil is a composed of essential polyunsaturated fatty acids: linoleic (70%) and (10%) gamma-linoleic acid (GLA), both series of omega 6, precursors of various cellular mediators used for the proper functioning and stability the membranes of cells in the body, the development of the nervous system, and the hormonal regulation of coagulation. Primrose further acts as a precursors of eicosanoids (prostaglandins, thromboxane, leukotriene and hydroxyl acids), compounds that regulate various biological processes through the human body. There is also a lesser extent oleic acid (monounsaturated fatty acid). Moreover, when the diet is lacking these essential fatty acids, it can generate conditions in the heart, circulation, skin, the immune system, reproductive system, and nervous system causing brain dysfunction. Therefore, the application of primrose oil can aid the human body with the intake of essential fats that address hair loss due to poor circulation, bacterial infections, inflammation, and the lack of protein.

In an example of horsetail, horsetail is a relatively older herbaceous perennial plants. It has separate sterile non-reproductive and fertile spore-bearing stems that grow from a perennial underground rhizomatous stem system. Horsetail is rich in minerals silicon (10%), potassium, and calcium. Silicon is generally classified as an element that is useful for plants' structure, physiology, and protection. Silicon is taken up by the roots in the form of silicic acid [Si (OH$_4$)], which is an uncharged monomeric molecule, when the solution pH is below 9% in use. Silicic acid is a soluble form of silicon and one of the basic form, which is absorbed and used by plants. The polymerized silicates is one of the hardest materials in this plants tissues. The silicon of the plant helps to raise the plant's health by creating a strong resistance and resistant structure to natural element damage. Research has demonstrated that the silicon in the horsetail has many beneficial factors including strengthening brittle nails and hair loss, as well as resistant to mold and various fungi.

In this way, the hair care product may comprise at least one of terpenes hydrocarbons (e.g., monoterpene, sesquiterpenes, etc.), oxygenated compounds (e.g., alcohol, monoterpene alcohol, etc.), aldehydes, ketones, esters, ethers, oxides, nettles, cypress, coconut oil, hemp oil, primrose (e.g., oleic acid, amino acids, vitamins, etc.), horsetail, and/or other compounds.

Further, unless specified otherwise, "first," "second," and/or the like are not intended to imply a temporal aspect, a spatial aspect, an ordering, etc. Rather, such terms are merely used as identifiers, names, etc. for features, elements, items, etc. For example, a first object and a second object generally correspond to object A and object B or two different or two identical objects or the same object.

Moreover, "exemplary" is used herein to mean serving as an example, instance, illustration, etc., and not necessarily as advantageous. As used herein, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes", "having", "has", "with", and/or variants thereof are used in either the detailed description or the claims, such terms are intended to be inclusive in a manner similar to the term "comprising".

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A method of making a hair care product consisting essentially of providing a coconut oil in a liquid state;
   mixing the coconut oil with a horsetail extract, a nettle leaf oil, a tee tree oil, and at least one of a lavender oil, a clary sage oil, a rosemary oil, a basil oil, a lemongrass oil, a cypress oil, a cinnamon leaf oil, or a roman chamomile extract to create a first mixture;
   microwaving the first mixture to bond the components together to create a second mixture; and
   mixing hemp oil or an evening primrose extract with the second mixture to create a third mixture which is the hair care product.

2. The method of claim 1, wherein:
   the lavender oil is used in an amount between about 0.02 ml to about 0.06 ml by volume;
   the tee tree oil is used in an amount between about 0.04 ml to about 0.08 ml by volume;
   the nettle leaf oil is used in an amount between about 0.04 ml to about 0.08 ml by volume;
   the horsetail extract in is used an amount between about 0.01 ml to about 0.05 ml by volume;
   the clary sage oil is used in an amount between about 0.02 ml to about 0.06 ml by volume;
   the rosemary oil is used in an amount between about 0.02 ml to about 0.06 ml by volume;
   the basil oil is used in an amount between about 0.02 ml to about 0.06 ml by volume;
   the lemongrass oil is used in an amount between about 0.02 ml to about 0.04 ml by volume;
   the cypress oil is used in an amount between about 0.02 ml to about 0.04 ml by volume;
   the cinnamon leaf oil is used in an amount between about 0.01 ml to about 0.03 ml by volume; and
   the roman chamomile extract is used in an amount between about 0.01 ml to about 0.03 ml by volume.

\* \* \* \* \*